United States Patent [19]
Sambursky

[11] Patent Number: 5,919,230
[45] Date of Patent: *Jul. 6, 1999

[54] INTRAOCULAR LENS IMPLANT AND METHOD OF MAKING SAME

[76] Inventor: Daniel Louis. Sambursky, 5 Riverside Dr., Apt. 806, Binghamton, N.Y. 13905

[ * ] Notice: This patent issued on a continued prosecution application filed under 37 CFR 1.53(d), and is subject to the twenty year patent term provisions of 35 U.S.C. 154(a)(2).

[21] Appl. No.: 08/819,263

[22] Filed: Mar. 18, 1997

[51] Int. Cl.⁶ .................................................. A61F 2/16
[52] U.S. Cl. .................................................. 623/6
[58] Field of Search .................................... 623/6

[56] References Cited

U.S. PATENT DOCUMENTS

| | | | |
|---|---|---|---|
| 4,424,597 | 1/1984 | Schlegel | 623/6 |
| 4,615,702 | 10/1986 | Koziol et al. | 623/6 |
| 4,834,750 | 5/1989 | Gupta | 623/6 |
| 5,047,051 | 9/1991 | Cumming | 623/6 |
| 5,180,390 | 1/1993 | Drews | 623/6 |
| 5,203,790 | 4/1993 | McDonald | 623/6 |
| 5,290,892 | 3/1994 | Namdaran et al. | 526/259 |
| 5,344,449 | 9/1994 | Christ et al. | 623/6 |
| 5,496,366 | 3/1996 | Cumming | 623/6 |
| 5,556,400 | 9/1996 | Tunis | 606/107 |

OTHER PUBLICATIONS

Chiron Vision Corporation, "Chiroflex" product information sheet, ©1996, 2 pages.

*Primary Examiner*—Randy C. Shay
*Attorney, Agent, or Firm*—Howrey & Simon; Daniel N. Daisak; Cono A. Carrano

[57] ABSTRACT

An intraocular lens implant including a lens optic portion, a haptic portion and a support structure formed with the lens implant. The support structure extending longitudinally along at least a portion of the implant. The intraocular lens can be implanted in the capsular bag or placed in the ciliary sulcus after cataract surgery.

20 Claims, 5 Drawing Sheets

INTRAOCULAR LENS IMPLANT AND METHOD OF MAKING SAME

BACKGROUND OF THE INVENTION

1. Field of the Invention

The invention relates generally to an intraocular lens and more particularly to an intraocular lens for implantation in the capsular bag or ciliary sulcus after removal of the human lens with cataract surgery.

2. Description of Related Art

Cataract surgery involves the replacement of an opacified crystalline human lens with an intraocular lens implant. A technique for removing the human lens, phacoemulsification, removes the nucleus and cortex of the opacified lens while leaving the thin transparent membrane known as the capsular bag virtually intact. Generally, a scleral or corneal incision is made and the nucleus of the cataract is emulsified preserving the capsular bag. The remaining cortex of the lens is then removed using irrigation and aspiration. Next, an intraocular lens is implanted in the capsular bag and the incision is closed. In patients where the posterior capsule has been compromised during surgery, an intraocular lens may also be positioned in the cillary silcus located in front of the anterior capsule and behind the iris portion of the eye.

The lens used for either capsular bag or cillary silcus implantation may be a hard lens, typically made from glass or plastic materials, or a foldable lens typically formed from silicone, acrylic, hydrogel or other soft materials. The size of the incision is proportional to the type of lens to be implanted. For example, if a hard lens is to be implanted in the capsular bag, usually a scleral incision is used and the incision size typically ranges from 5.5 mm to 7.0 mm. Implantation of a hard lens in the cillary silcus requires an incision size of approximately 6.0 mm. However, a hard lens is incapable of being folded or otherwise manipulated for insertion through a relatively small incision as compared with the incision size required for a foldable lens. Generally, a smaller incision is preferred because of the advantages associated therewith which include greater wound stability, decreased induced astigmatism, more rapid visual and physical rehabilitation as well as reduction of associated medical and surgical expenses.

A foldable lens, on the other hand, can be used with a scleral or corneal incision and typically only requires an incision size of within the range of approximately 2.5 to 4.0 mm depending on the type of foldable lens selected. The foldable lens is compressed or folded along its longitudinal dimension, inserted through the incision, positioned within the capsular bag, and passively unfolded in the capsular bag or cillary silcus such that the lens optic portion is centered.

In its uncompressed position, a foldable lens is typically within the range of approximately 5.5–6.5 mm wide and has a longitudinal dimension of approximately 12.0 to 13.0 mm. However, in its compressed or folded position, the foldable lens is capable of passing through the approximately 2.5 to 4.0 mm incision. Typically, there are two types of foldable lenses used for cataract implantation. First, a plate lens includes an optic portion and plate haptic portions usually formed from silicone. The plate lens is folded longitudinally, inserted through the incision and positioned within the capsular bag. An injector may be used to deliver the plate lens through the wound and into position. When a plate lens is inserted into the capsular bag, the lens centers well, however over time, the lens tends to de-center due to scaring and fibrosis of the capsular bag. Another disadvantage associated with the plate lens is that because the capsular bag may contract asymmetrically, a typical plate lens may bend or sublaxate within the bag thereby changing the refractive effect of the lens. This induces unintended hyperopia, myopia or astigmatism. Another drawback associated with the plate lens occurs after laser capsulotomy, a procedure which creates an opening in the posterior capsule after cataract surgery in patients where the capsule opacifies and causes decreased vision. Specifically, because the lens is not sufficiently rigid, the lens may fold back-up due to contraction of the capsular bag and be extruded through the posterior capsular opening and into the vitreous cavity requiring corrective surgery. Another drawback associated with a plate lens is that a continuous circular opening is required to facilitate implantation. If the opening is non-continuous or jagged, the plate lens becomes unsuitable for implantation in the capsular bag because lens delivery will result in tears of the anterior capsule portion which results in inadequate fixation of the lens. A still further disadvantage with the plate lens is evident in this type of lens cannot be used for implantation in the cillary silcus. In particular, because the longitudinal size of the cillary silcus, usually approximately 13.0 mm, is larger than the longitudinal size of the plate lens which is usually approximately 12.0 mm, decentration of the lens optic portion occurs causing vision degeneracy, and therefore, a plate lens is contra-indicated for silcus implantation.

A second type of foldable lens typically used is referred to as a three piece lens. This type of lens usually includes a lens optic portion and a pair of J-shaped or C-shaped loop haptics connected to the optic portion at separate juncture sites located along the peripheral edge of the optic. The optic portion may be made of acrylic, silicone or other foldable materials. The haptic portion of the lens typically is made of polymethylmethacrylate (PMMA) or polypropylene (Prolene).

Similar to the plate lens, the three piece lens may be folded, inserted through an incision and positioned within the capsular bag. Typically, the incision size required for insertion of a three piece lens is approximately 3.0–4.2 mm. However, a disadvantage associated with the three piece lens is that it is more awkward to handle than the plate lens which makes positioning within the capsular bag more cumbersome and may result in damage to the lens, haptics or intraocular tissue during implantation. In addition, the incision size required for insertion is approximately 3.0 to 4.2 mm whereas a plate lens may be used with an incision of approximately 2.5 to 4.0 mm. Another disadvantage associated with the three piece lens is that when implanted in the capsular bag, it may decenter because the loop haptics tend to have low tensile strength to permit folding, but not sufficiently rigid to maintain positioning after insertion. This may result in decentering because of capsular fibrosis and contraction. Likewise, the three piece lens is not the preferred choice for lens implantation in the cillary silcus because of the lens' insufficient rigidity. A further disadvantage associated with the three piece lens is that bacteria tends to migrate at the juncture or connection sites between the optic and haptic portions thereby increasing the potential for post-operative infection.

SUMMARY OF THE INVENTION

The invention meets these needs and avoids the disadvantages and drawbacks of the above-described prior art by providing a lens implant which includes a lens optic portion, a haptic plate portion and a support beam that extends longitudinally along at least a portion of the peripheral edge of the implant. The lens implant can be compressed and inserted through a relatively small incision and capable of maintaining its position within the capsular bag or ciliary silcus after insertion.

The intraocular lens implant is formed from sufficiently flexible material to provide foldability to take advantage of the incision used during phacoemulsification without the need to increase wound size. The lens optic portion is preferably formed from silicone or other flexible material which includes refractive index properties inherent for vision correction. The haptic portion can be formed with the lens optic portion and extends outwardly therefrom.

The lens implant includes one or more support beams which prevents the lens, once implanted, from folding back-up and extruded through the posterior capsular opening requiring corrective surgery. The one or more support beams provides a rigid support for the lens structure while allowing the lens implant to be folded along its longitudinal axis to accommodate implantation through cataract incision. The one or more support beams can be integrally formed within the lens implant. The support beam can also be formed on the anterior and/or posterior surfaces of the lens. Each beam extends longitudinally at least a portion of the length of the lens implant.

The foregoing, and other features and advantages of the present invention, will be apparent from the following more particular description of the preferred embodiments, the accompanying drawings and the appended claims.

DETAILED DESCRIPTION

Figure 1:
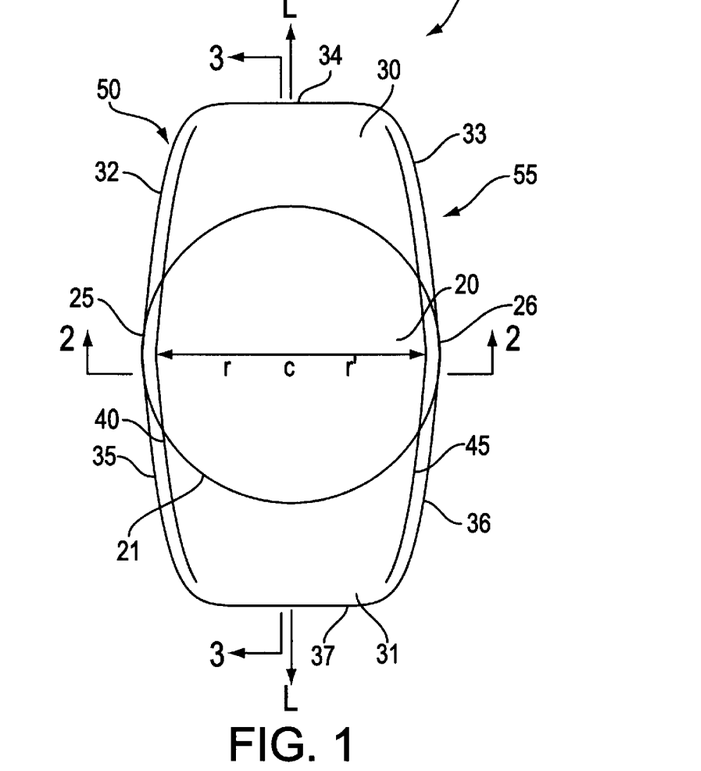
FIG. 1 is a plan view schematically illustrating an intraocular lens in which a pair of support beams extend along the length of the lens implant in accordance with the principles of the invention.

The preferred embodiments of the present invention are now described with reference to figures where like reference numbers indicate like elements. Referring first to FIG. 1, the principles of the invention are illustrated in this schematic view of an intraocular lens 10, which generally includes an optic lens portion 20 and haptic plate portions 30 and 31. As will be more apparent from the drawings and detailed description below, the length of the intraocular lens 10 is proportional to the interior dimensions of the capsular bag and/or the cillary silcus thereby substantially reducing the possibility of decentering in these regions. Although the intraocular lens is shown as having a generally rectangular shape, it is understood that alternative shapes may be employed which embody the principles of the present invention as the skilled artisan will appreciate.

The lens may be formed from flexible plastics, such as silicon or acrylic, as well as other similar materials which permit folding or compression of the lens for insertion into the capsular bag through the cataract incision used during phacoemulsification. The folded or compressed lens fits through an incision which is preferably between approximately 2.5–3.2 mm which is considered relatively small, thereby taking advantage of the attributes associated with smaller incision techniques such as that which is described above. The folded lens may also be employed with insertion into the capsular bag by use of injection techniques known in the art. In addition, in cases of non-continuous anterior capsular openings, the lens implant in accordance with present invention can be placed within the capsular bag and can resist asymmetric contracture of the capsular bag because of the support structure described herein. In cases of non-continuous capsular openings, the capsular bag tends to contract asymmetrically resulting in decentration of the lens. The support structure of the present invention resists these asymmetric capsular forces.

The optic lens portion 20 has a substantially circular shape having a diameter within the range of approximately 5.5 to 6.3 mm. The optic portion may be formed, in a conventional manner, from silicone, acrylic, other hydrophilic polymers, hydrogels, or thermolabile materials. The optic portion has a perimeter 21 which is integrally formed with the haptic plate portions 30 and 31. The thickness of the optic lens is dependent on the refractive index of the lens material and the lens power needed for a particular patients vision requirements. For example, the more farsighted a person is preoperatively, the greater the lens power needed to correct the patients vision and the thicker the intraocular lens. The refractive index of the material used will inversely correlate to the lens thickness.

The plate haptic portions 30 and 31 of the lens implant 10 assist in the retention of the implant in the capsular bag. In this preferred embodiment, the plate haptics are integrally formed with lens optic portion 20 and extend outwardly therefrom. The plate haptics are preferably formed from the same material selected for forming the optic lens portion. This integral formation between the plate haptics and the lens optic portion reduces the chances of infection by eliminating a site for bacteria migration. As shown in FIG. 1, plate haptic portion 30 is defined by longitudinal walls 32 and 33 and side wall 34. Likewise, plate haptic portion 31 is defined by longitudinal walls 35 and 36 and side wall 37. From the foregoing description, it is readily apparent that longitudinal wall 50 of the lens implant 10 is defined by haptic longitudinal walls 32 and 35 and a portion of the lens perimeter 25; and longitudinal wall 55 of lens implant 10 is defined by haptic longitudinal walls 33 and 36 and a portion of the lens perimeter 26. The longitudinal walls 50 and 55 of the lens implant, preferably have a generally arcuate shape. However, these longitudinal walls may also take on alternative shapes which embody the principles of the invention.

In this preferred embodiment, a semi-rigid support structure is integrally formed with the lens implant to provide lens stability. The support structure, for example, can be in the form of support beams 40 and 45 integrally formed within the plate haptic portions 30 and 31 and lens optic portion 20. These beams may also be formed on the anterior and/or posterior surfaces of the lens implant as shown with reference to FIGS. 8A and 8B. The support beams 40 and 45 are formed from a rigid or semi-rigid material such as PMMA. The support beams 40 and 45 extend substantially the length of lens 10 from plate haptic portion 30 to plate haptic portion 31. Each support beam can have a thickness in the range of 0.05 mm to 0.2 mm thick. However, as will be described below, alternative support structure configurations as well as haptic portions can be employed without departing from the spirit and scope of the present invention.

Support beams 40 and 45 extend along longitudinal walls 50 and 55 distances r and r' from the center C of the lens optic portion 20. In this manner, the lens optic portion remains substantially unobstructed while allowing the support beams to extend along the longitudinal walls of the lens implant. This avoids compromising the refractive function of the lens optic portion 20 while allowing the beams to support the lens implant structure. The distances r and r' may preferably be within the range of approximately 2.6–3.15 mm. The support beams can be made of a clear or colored PMMA or semi-rigid material to facilitate placement of the lens 10 in the capsular bag or cillary sulcus. Because the rigidity provided by the support structure, the lens optic diameter can be reduced without risk of decentration.

Figure 2:
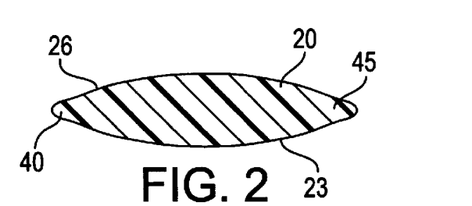
FIG. 2 is a cross-sectional view taken along lines 2—2 of FIG. 1 illustrating a pair of beams within the haptic plate.

Turning now to FIG. 2, a cross-section taken along lines 2—2 of the lens shown in FIG. 1, obviously not drawn to scale, illustrates a preferred embodiment of the present invention where the placement of support beams 40 and 45 are formed within the structure of the lens implant 10. In this manner, juncture sites in which microorganisms can harbor are eliminated. The thickness and tensile strength of each support beam 40 and 45 is sufficient to provide adequate rigidity for the lens implant 10 to maintain its unfolded longitudinal structure once implanted while substantially preventing latitudinal folding. Each beam can have a variety of shapes such as square, round, oval, rectangular, planar, however, alternative shapes and structures are possible without departing from the scope and spirit of the invention.

Figure 3:
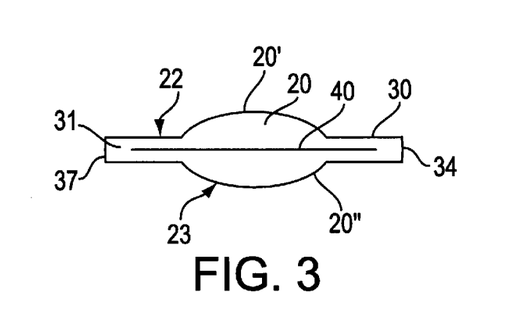
FIG. 3 is a schematic view taken along lines 3—3 of the lens shown in FIG. 1

FIG. 3 is a schematic view taken along lines 3—3 of the lens shown in FIG. 1, obviously not drawn to scale, illustrating a longitudinal cross section of the lens implant. Support beam 40 extends substantially the length of the implant from haptic portion 30 to haptic portion 31. The optic portion 20 is defined by an anterior rounded portion 20' and a posterior rounded portion 20" each of which extend from haptic portions 30 and 31. Support beams 40 (and 45, not shown) can also extend the entire length of lens implant 10, from side wall 34 to side wall 37.

Figure 4:
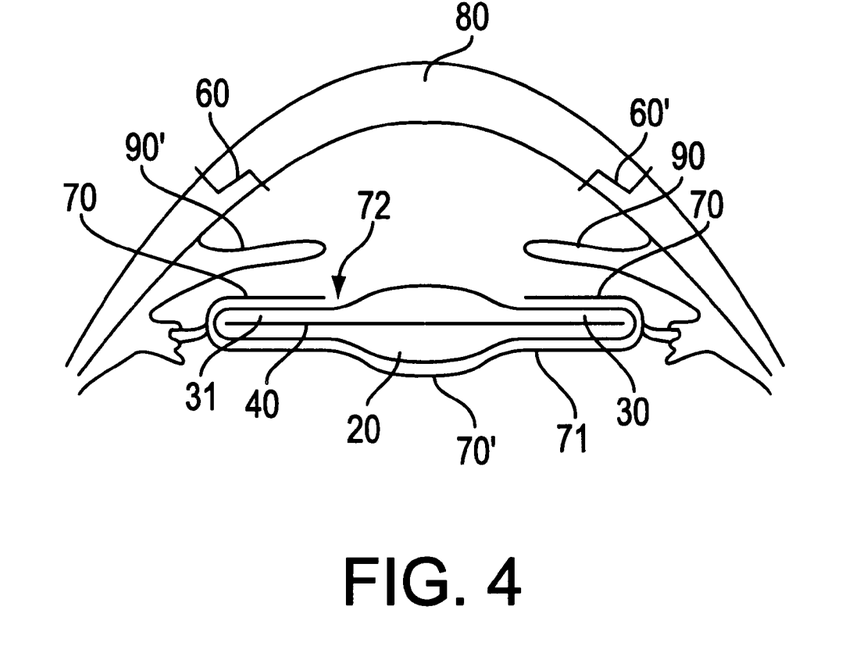
FIG. 4 is a cross-sectional view of the human eye shown schematically and illustrating the placement of the intraocular lens of FIG. 1 implanted within the capsular bag.

FIG. 4 illustrates a cross-sectional view of the human eye with lens implant 10 positioned within the capsular bag defined by anterior portions 70 and posterior portion 70'. FIG. 4 generally illustrates the iris portions 90 and 90', cornea 80, anterior portion of the capsular bag 70 and the posterior portion of the capsular bag 70' after the nucleus and cortex have been removed by cataract surgery. An opening has been formed in the anterior capsule 70 to facilitate emulsification of the lens nucleus and irrigation/aspiration of the lens cortex leaving the posterior capsule 70' intact. A scleral incision 60 or a corneal incision 60' may be used for lens implantation. As the lens implant 10 is prepared for insertion, the lens is folded along its longitudinal axis L shown with reference to FIG. 1. In this manner, the lens may be folded and inserted through the same incision used during phacoemulsification. The lens, in its folded or compressed position may be inserted through the opening 72 between anterior capsular bag portions 70 by injection, and/or other insertion techniques. Once in the capsular bag, the lens 10 passively unfolds and plate haptic portions 30 and 31 communicate with the interior surface 71 of the posterior capsular bag 70' and anterior capsular bag portions 70. Lens optic portion 20 is substantially centered within the capsular bag and is aligned with the visual axis of the eye. Support beam 40 (and 45, not shown in FIG. 4) provide a rigid longitudinal support for the lens 10 within the capsular bag. Latitudinal flexation of the lens 10 with the posterior bag portion 70' tends to be nominal with the width of the lens in the range of approximately 5.5 mm to approximately 6.3 mm as compared with the width of the bag which is approximately 10.5 mm.

The support beam structure of the present invention reduces the possibility of decentration or induced refractive change because the beams resist folding or compression of the implant by fibrosis of the capsular bag. Fibrosis may occur but the lens will have the imparted tensile strength of the support beam and resists contracture. The added rigidity of the lens provided by the support beams allow the posterior capsule to be pulled in tight apposition to the lens optic to prevent opacification of the posterior capsule. Moreover, the support beams prevent dislocation of the lens into the vitreous cavity after laser capsulotomy as will be described in more detail below with reference to FIG. 5.

Figure 5:
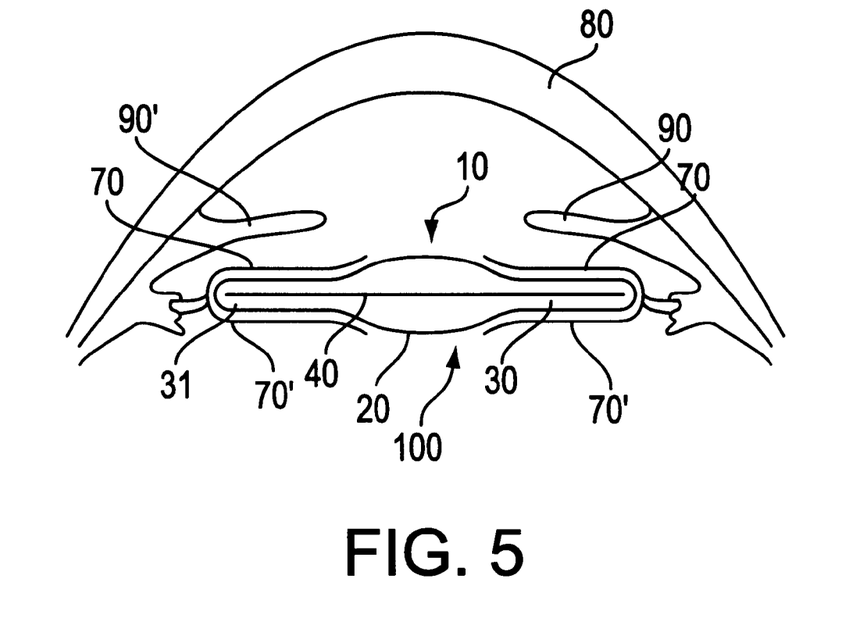
FIG. 5 is a cross-sectional schematic view of the human eye illustrating the implantation of the intraocular lens of FIG. 1 after the posterior portion of the capsular bag has been opened with laser capsulotomy.

FIG. 5 illustrates a cross-sectional view of the human eye with lens implant 10 positioned in the capsular bag defined by anterior portions 70 and posterior portion 70', however, the posterior portion of the capsular bag has been intentionally opened with laser capsulotomy. Approximately 20–30% of patients develop opacification of the posterior capsule following cataract surgery ranging from months to years after surgery. An opening is made in the posterior capsule, between posterior portions 70', which then gives the patient an optically clear zone to see. Prior art lenses, without the advantages of the support structure in accordance with the present invention, may dislocate into the vitreous cavity 100 located behind posterior portions 70' of the capsular bag because the lens would tend to fold secondary to contraction and fibrosis of the capsular bag. This could cause complications which necessitates corrective surgery. However, the present invention includes support beam(s) 40 (and 45, not shown in FIG. 5) which provide longitudinal support for the lens 10. This support beam structure prevents dislocation of the lens 10 into the vitreous cavity 100 after laser capsulotomy thereby preventing further patient surgery.

Figure 6:
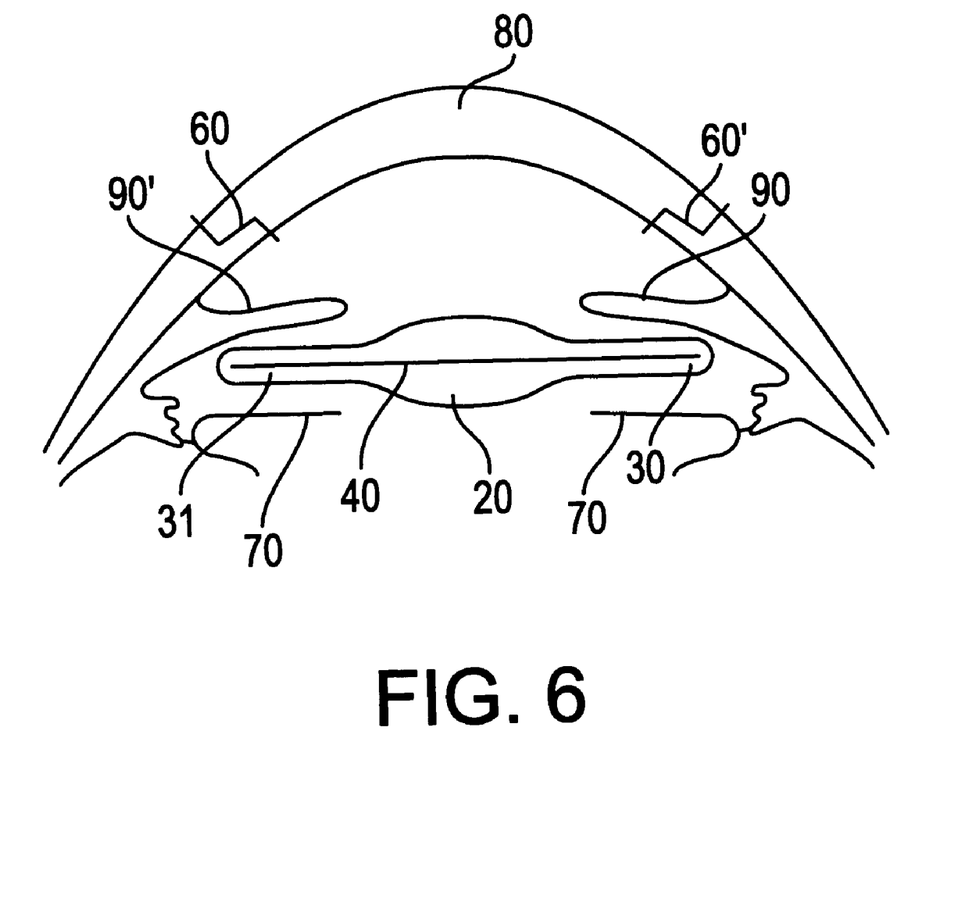
FIG. 6 is a cross-sectional view of the human eye shown schematically and illustrating the placement of the intraocular lens of FIG. 1 implanted in the cillary silcus.

Turning now to FIG. 6, which is also a cross-sectional view of the human eye, however the lens implant 10 is positioned in the cillary silcus which is the area of the eye located in front of the anterior portion 70 of the capsular bag and behind iris portions 90 and 90'. Incisions 60 or 60' may be employed for insertion of the lens implant after cataract surgery. This type of lens implantation is necessitated when the posterior capsule 70' has been compromised thereby preventing insertion of the implant within the capsular bag. The support beam(s) 40 (and 45 not shown in FIG. 6) provides a rigid support for the lens 10 within the cillary silcus region. Plate haptic portions 30 and 31 are in close proximity to iris portions 90 and 90', respectively. The lens optic portion 20 is generally centered within the cillary silcus for proper vision correction. The support beams 40 (and 45) substantially prevents decentration of the lens optic portion within the cillary silcus.

Figures 7, 8, 8A, 8B:
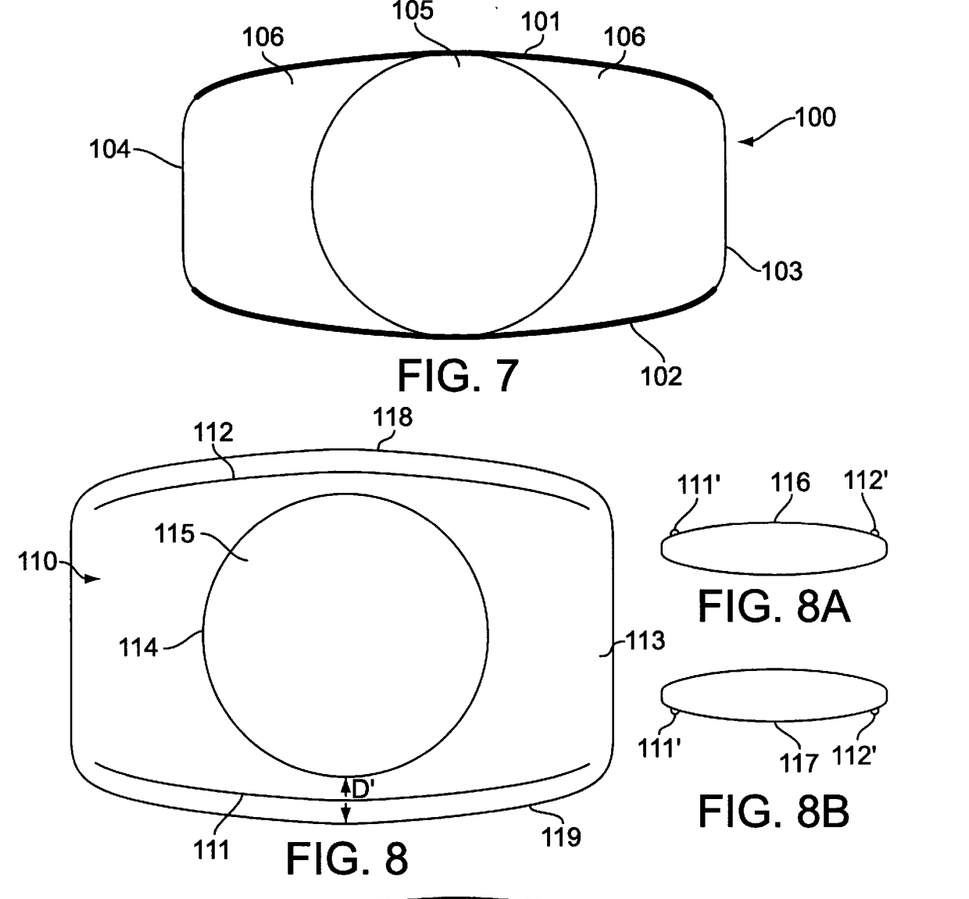
FIGS. 7–12 are plan views schematically illustrating alternative embodiments of the support beam structure of the intraocular lens in accordance with the present invention.

FIGS. 7 through 12 illustrate alternative embodiments of the support beam structure in accordance with the present invention. These alternative lenses may also be implanted in the human eye as described with reference to FIGS. 4–6 above and include the features and attributes associated therewith. Turning now to FIG. 7 which is a top plan view of a lens implant 100 with lens optic portion 105, and haptic portions 106, the support beams 101 and 102 define the longitudinal side walls of the lens implant 100. In this embodiment, the support beams 101 and 102 extend the length of the lens 100 and side walls 103 and 104 complete the generally rectangular shape.

FIG. 8 illustrates the lens implant 110 which includes support beams 111 and 112 that extend longitudinally along the lens implant 110 within the unitary plate haptic portion 113. The haptic portion 113 is integrally formed with the peripheral edge 114 of lens optic portion 115 and extends around the optic portion 115. The longitudinal walls 118 and 119 of the lens implant 110 are defined by the perimeter of the haptic portion 113. Support beams 111 and 112 extend longitudinally along the haptic portion within space D' which is the distance between the peripheral edge of optic portion 115 and the longitudinal walls 118 and 119 of implant 110. This configuration allows the support beam structure to provide rigidity to the lens implant while not interfering with the periphery of lens optic portion 115. Alternatively, the support beams 111' and 112' can be formed on the anterior surface 116 of the lens as shown in FIG. 8A or on the posterior surface 117 of the lens implant as shown in FIG. 8B. Support beams 111' and 112' are integrally formed with the anterior and posterior surfaces, respectively in order to prevent the formation of juncture sites which increase the possibility of infection.

Figure 9:
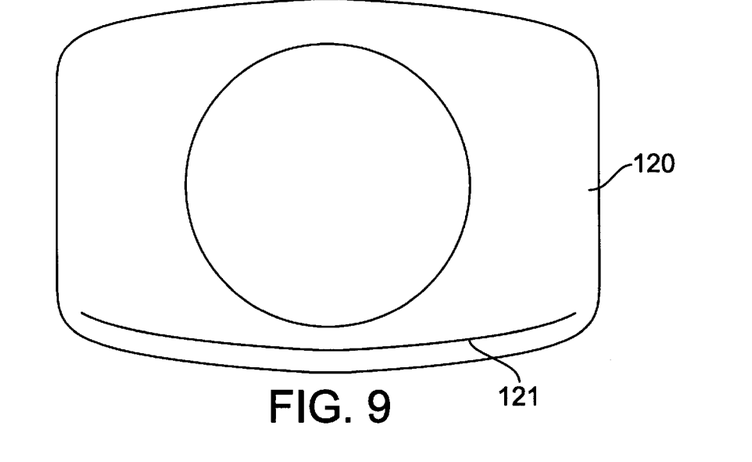

FIG. 9 illustrates the lens implant 120 which includes a single support beam 121 which extends substantially the length of the implant. The single support beam provides sufficient rigidity to prevent the implant 120 from dislocating into the vitreous cavity. Similarly, the support beam 121 also provides sufficient support for the lens structure when implanted in the cillary silcus. As would be clearly apparent to one skilled in the art, beam formations within the implant structure and on the anterior and posterior surfaces or any combination thereof can be employed in accordance with the present invention.

Figure 10:
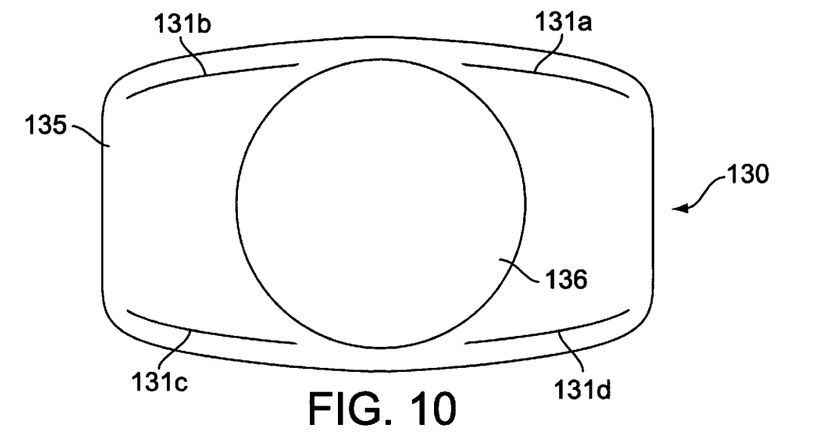
Figure 11:
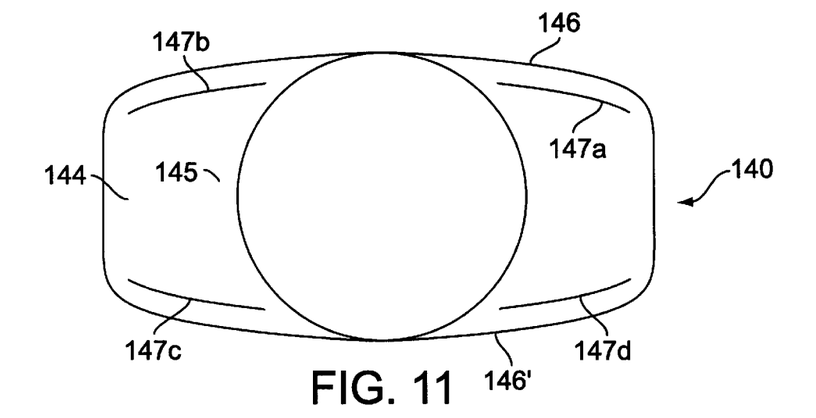

FIGS. 10 and 11 illustrate the lens implant of the present invention with alternative support beam configurations. FIG. 10 shows a lens implant 130 which is similar to that which is shown in FIG. 8 with respect to the haptic portion which extends around the perimeter of lens optic 136. However, lens implant 130 includes support beams 131a, 131b, 131c, and 131d which are formed in unitary plate haptic portion 135 and provide support to the lens implant. Likewise, FIG. 11 shows a lens implant 140 which is similar to the embodiment shown in FIG. 1 with respect to the lens optic portion 145 forming part of the longitudinal walls 146 and 146' of the lens implant. However, the embodiment of FIG. 11 illustrates the plate haptic 149 including support beams 147a, 147b, 147c and 147d. In this manner, each of the support beams extend, longitudinally, along a portion of plate haptic 149 and avoid lens optic portion 145.

Figure 12:
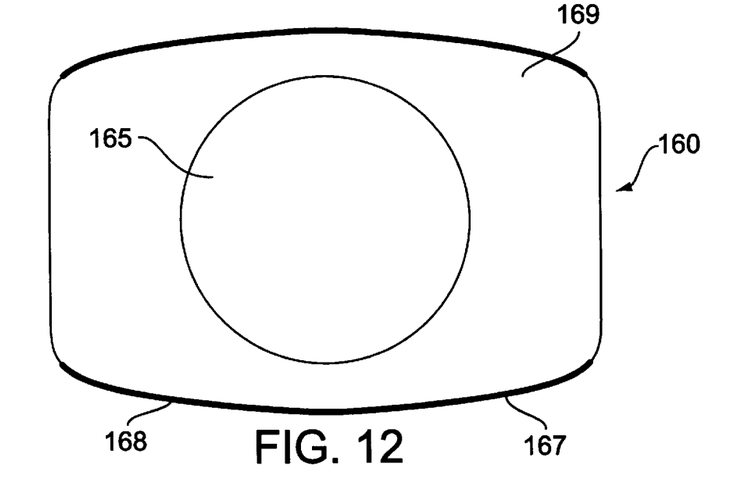

Similarly, FIG. 12 shows an embodiment of the lens implant 160 where the lens optic portion 165 is integrally formed with plate haptic portion 169. Longitudinal side wall 168 is defined by support beam 167. The support beam structure prevents the implant from dislocating into the vitreous cavity and provides sufficient support for implantation in the cillary silcus.

While the present invention has been particularly shown and described with reference to several preferred embodiments thereof, it will be understood by those skilled in the art that various changes in form and details may be made therein without departing from the spirit and scope of the present invention as defined in the appended claims.

What is claimed is:

1. An intraocular lens implant comprising:
   a substantially circular lens optic portion having an outer perimeter;
   a first plate haptic portion extending outwards in a first direction from said outer perimeter of said lens optic portion;
   a second plate haptic portion extending outward in a second direction diametrically opposite said first direction from said outer perimeter of said lens optic portion;
   said lens optic portion and said first and second plate haptic portions defining a longitudinal axis; and
   a substantially rigid support beam system configured to resist asymmetric capsular forces and allowing longitudinal folding of said intraocular lens implant for eye insertion, said support beam system including a first support beam integrally formed within said first plate haptic portion, said lens optic portion and said second plate haptic portion, said first support beam only extending parallel to said longitudinal axis from said first plate haptic portion, through said lens optic portion into said second plate haptic portion, wherein all portions of said substantially rigid support beam system extend only in a longitudinal direction.

2. The intraocular lens implant in accordance with claim 1 wherein said lens intraocular implant has a generally rectangular shape, said optic portion being generally centered within said lens implant.

3. The intraocular lens implant of claim 2 wherein said rectangular shape is defined by first and second longitudinal outer walls comprising portions of said first haptic portion, said optic perimeter and said second haptic portion, and first and second latitudinal outer walls defined by a portion of either said first or second haptic portions, respectively said latitudinal outer walls connecting said first and second longitudinal outer walls.

4. The intraocular lens implant of claim 1 having an anterior surface wherein said support structure is formed on said anterior surface.

5. The intraocular lens implant of claim 1 having a posterior surface wherein said support structure is formed on said posterior surface.

6. The intraocular lens implant in accordance with claim 1 wherein said first support beam extends longitudinally substantially the entire length of said implant.

7. The intraocular lens implant in accordance with claim 1 wherein said support beam 0.05 to 0.2 mm thick.

8. The intraocular lens implant of claim 1 wherein said support structure extends on said haptic portion.

9. The intraocular lens implant of claim 1 further including a second haptic portion wherein said support structure extends on said second haptic portion.

10. The intraocular lens implant of claim 1 further including a second haptic portion wherein said support structure extends on said haptic portion and said second haptic portion.

11. The intraocular lens implant of claim 1 wherein said lens optic portion is made from at least one material selected from the group consisting essentially of silicone, acrylic, hydrophilic polymer, hydrogel, and thermolabile materials.

12. The intraocular lens implant of claim 1 wherein said lens implant is made from flexible plastics selected from the group consisting essentially of silicone and acrylic.

13. The intraocular lens implant in accordance with claim 1 wherein said second support beam is transversely separated from said first support beam a predetermined distance.

14. The intraocular lens implant of claim 1 wherein said first and second haptic portions and a portion of said lens optic portion define a longitudinal perimeter, said first support beam transversely separated, within said first and second haptic portions and said lens optic portion, a distance from said longitudinal perimeter.

15. The intraocular lens implant of claim 1 wherein said support beam system further includes a second support beam integrally formed within said first plate haptic portion, said lens optic portion and said second plate haptic portion, said second support beam only extending parallel to said longitudinal axis from said first plate haptic portion, through said lens optic portion into said second plate haptic portion.

16. An intraocular lens implant comprising:

a lens optic means for providing corrective vision;

a plate haptic means for providing alignment of said lens implant, said plate haptic means integrally formed with said lens optic means and extending outward from said lens optic means, said lens optic means and said plate haptic means defining a longitudinal axis of said intraocular lens implant; and a support means for providing longitudinal support for said lens implant, said support means integrally formed in said lens optic means and said plate haptic means, said support means only extending longitudinally along at least a portion of said plate haptic means and through said lens optic means such that said support means allows folding of said intraocular lens implant only along said longitudinal axis.

17. The intraocular lens implant of claim 16 wherein said support means is a first support means, said lens implant further comprising a second support means integrally formed in said lens optic means and said plate haptic means, said second support means only extending longitudinally along at least a portion of said plate haptic means and through said lens optic means.

18. The intraocular lens implant of claim 17 wherein said support beam extends on said haptic means.

19. The intraocular lens implant in accordance with claim 17 wherein said first support means includes a first support beam, said second support means includes a second support beam.

20. The intraocular lens implants of claim 16 wherein said support means extends longitudinally substantially the length of said implant.

* * * * *